United States Patent [19]

Pinnaduwage

[11] Patent Number: 5,896,196
[45] Date of Patent: Apr. 20, 1999

[54] PLASMA MIXING GLOW DISCHARGE DEVICE FOR ANALYTICAL APPLICATIONS

[75] Inventor: Lal A. Pinnaduwage, Knoxville, Tenn.

[73] Assignee: Lockheed Martin Energy Research Corporation, Oak Ridge, Tenn., TN

[21] Appl. No.: 08/912,907

[22] Filed: Aug. 15, 1997

[51] Int. Cl.[6] .......................... G01J 3/443; G01N 21/62
[52] U.S. Cl. .................... 356/311; 356/314; 356/316; 250/288
[58] Field of Search .............................. 356/311, 314, 356/316; 250/281, 288

[56] References Cited

PUBLICATIONS

Sato et al., "Electron–temperature control by movable pins installed in a hollow cathode for discharge plasma", *Appl. Phys. Lett.* 62(6) pp. 567–569, (1993).
Iizuka et al., "Effect of electron temperature on negative hydrogen ion production in a low–pressure AR discharge plasma with methane", *Appl.Phys.Lett.* 62 p. 1619 (1993).
Iizuka et al., "Enhanced methyl–radical production in an Ar–CH4 pin hollow cathode discharge", *Appl.Phys.Lett.* 64 pp. 1786–1788 (1994).

*Primary Examiner*—F. L. Evans
*Attorney, Agent, or Firm*—Quarles & Brady

[57] ABSTRACT

An instrument for analyzing a sample has an enclosure that forms a chamber containing an anode which divides the chamber into a discharge region and an analysis region. A gas inlet and outlet are provided to introduce and exhaust a rare gas into the discharge region. A cathode within the discharge region has a plurality of pins projecting in a geometric pattern toward the anode for exciting the gas and producing a plasma discharge between the cathode and the anode. Low energy electrons (e.g. <0.5 eV) pass into the analysis region through an aperture. The sample to be analyzed is placed into the analysis region and bombarded by the metastable rare gas atoms and the low energy electrons extracted into from the discharge region. A mass or optical spectrometer can be coupled to a port of the analysis region to analyze the resulting ions and light emission.

20 Claims, 1 Drawing Sheet

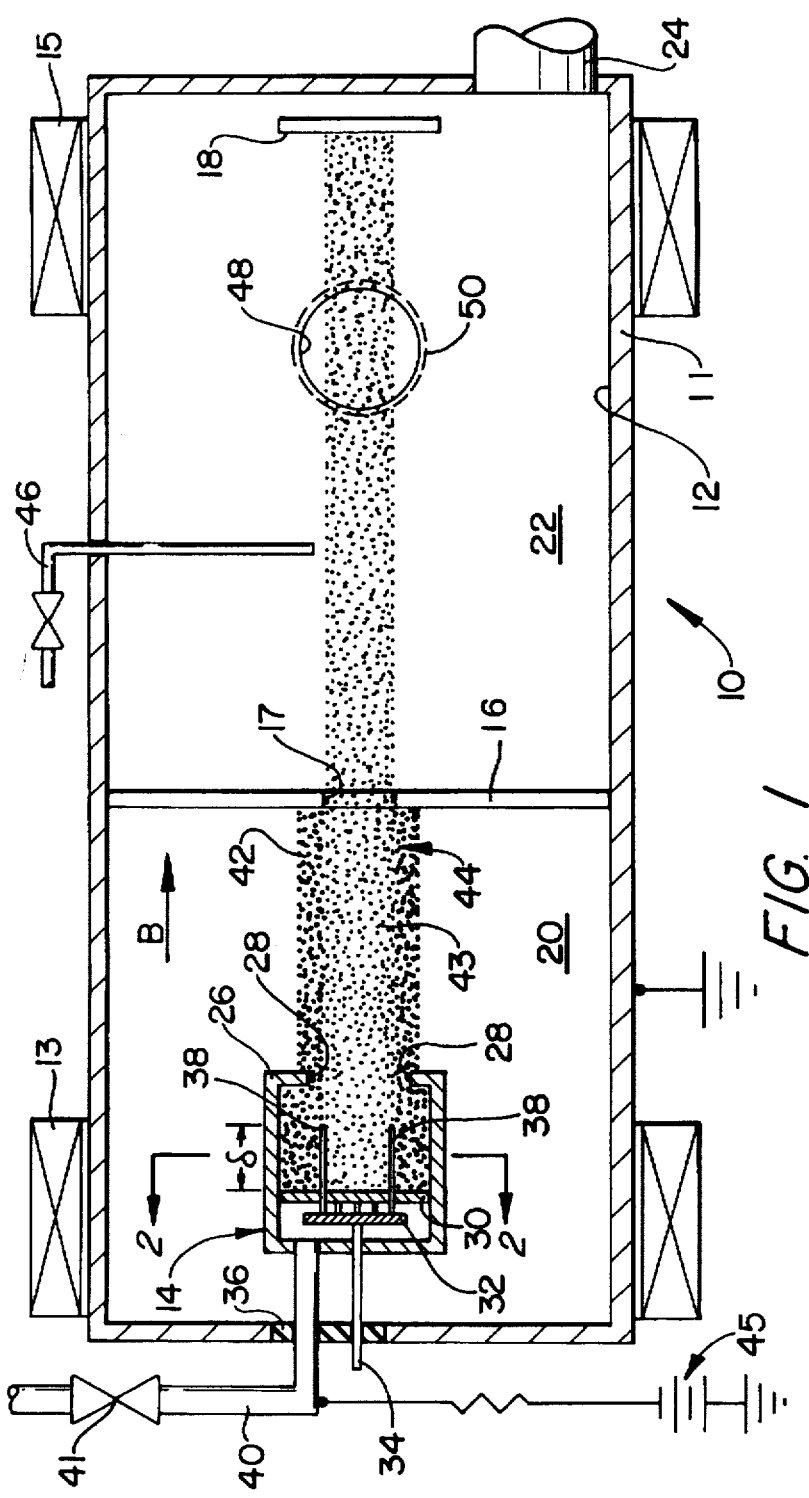
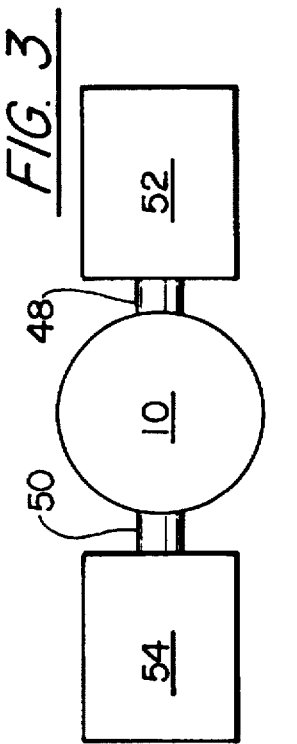
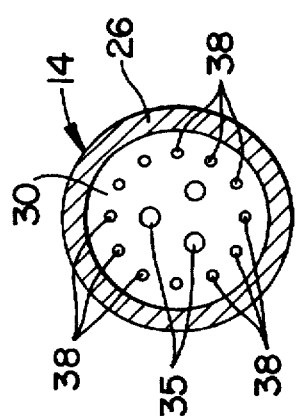

PLASMA MIXING GLOW DISCHARGE DEVICE FOR ANALYTICAL APPLICATIONS

This invention was made with government support under contract DE-AC05-96OR22464 awarded by the U.S. Department of Energy to Lockheed Martin Energy Research Corporation, and the United States Government has certain rights in this invention.

BACKGROUND OF THE INVENTION

The present invention relates to instruments for analyzing a sample to determine its identity and constituents; and more particularly to such instruments which excite the sample in a glow discharge apparatus for subsequent analysis by a mass spectrometer or an optical spectrometer.

In many industrial and environmental situations, it is desirable to analyze a sample of a substance to determine the presence and relative concentrations of the constituent materials in the substance. A common apparatus for performing such analysis is a mass spectrometer which involves bombarding the sample in the gas phase with a beam of medium-energy electrons in a high vacuum. Typically an electron gun is utilized as a source of bombarding electrons. The mass of charged particles and fragments produced by that bombardment then is determined, as described by J. D. Roberts et al., *Organic Chemistry methane to macromolecules*, pp. 158–159, 1971, W. A. Benjamin, Inc.

Another type of spectrometry involves exciting the sample so that it emits light in the ultra violet, visible and/or infrared wavelengths. By analyzing the specific wavelengths emitted by the sample, a determination of the constituents can be made. Several techniques have been utilized for exciting materials including combustion and introduction into a glow discharge chamber where the sample in the gas phase is exposed to an electric discharge. Unfortunately, that excitation often destroyed the sample which in many instances is undesirable.

Present industrial and environmental issues often require analytical techniques with very high sensitivity and wide applicability. Detection of trace levels at or below part-per-million (ppm) levels are routinely required in many regulatory analysis. In certain cases, such as detection of PCB's, analytical techniques capable of distinguishing between harmful and harmless homologs are not available. Thus it is desirable to analyze constituents of a material based on negative ion formation via electron attachment to electronically excited molecules which has a very high efficiency and also is expected to occur in the vast majority of chemicals. In addition, information is desirable on the formation of positive ions and about emission characteristics of the given sample. An instrument which can provide all of this information would be particularly useful.

SUMMARY OF THE INVENTION

The general object of the present invention is to provide a glow discharge apparatus for exciting a sample for analysis, wherein the sample is not directly exposed to an electric discharge.

Another object is to provide such a glow discharge device in which the capability of analyzing positive ion formation, negative ion formation, and light emissions can be incorporated into a single instrument to provide fast and accurate identification of trace elements.

A further object of the present invention is to provide an apparatus which produces negative ion formation by electron attachment to an electronically-excited states of the sample, with extremely high efficiency compared to conventional negative ion formation processes.

Yet another object of the present invention is to utilize a pin-hollow cathode in the glow discharge analytical instrument.

These and other objectives are satisfied by a glow discharge apparatus that prepares a sample for analysis. The apparatus includes an enclosure forming a chamber which contains an anode that divides the chamber into a discharge region and an analysis region. A cathode, associated with the discharge region, preferably has a plurality of pins projecting in a geometric pattern, such as a circle, toward the anode. An inlet enables a gas to be fed into the discharge region and a gas exhaust port also is provided, preferably in the analysis region so that the gas flows through those regions.

A mechanism is included by which the sample to be analyzed is introduced into the analysis region for bombardment by lower energy electrons extracted from the discharge region. For example, this mechanism may comprise an inlet port through the sample in the gas phase is supplied to the analysis region. A port, which opens into the analysis region, is provided for coupling to a device, such as a mass spectrometer or an optical spectrometer, that analyzes results of bombardment of the sample by the lower energy electrons.

This construction of the glow discharge apparatus separates the sample being analyzed from the discharge region and thus the sample is not exposed to the electrical discharge that occurs between the cathode and the anode.

BRIEF DESCRIPTION OF THE DRAWINGS

FIG. 1 is a cross sectional view through a glow discharge apparatus according to the present invention;

FIG. 2 is a cross section along line 2—2 of FIG. 1; and

FIG. 3 depicts the glow discharge apparatus connected to a mass spectrometer and an optical spectrometer.

DETAILED DESCRIPTION OF THE INVENTION

With initial reference to FIG. 1, a glow discharge apparatus 10 has an enclosure 11 that forms an air-tight chamber 12 containing a pin type hollow cathode 14, an anode 16 and a third electrode 18. The anode 16 divides the chamber 12 into a discharge region 20 in which the cathode 14 is located and an analysis region 22 on the other side of the anode 16. An aperture 17 extends through the anode allowing gases to flow between regions 20 and 22. An exhaust port 24 communicates with the analysis region 22 through the wall of the enclosure 11 and is connected externally to a conventional exhaust pump for gas discharge devices. A first electromagnet coil 13 is around the discharge region 20 and a second electromagnet coil 15 extends around the analysis region 22. These coils 20 and 22 produce a magnetic field B within the chamber 12.

With additional reference to FIG. 2, the cathode 14 includes a hollow, metal housing 26 with an opening 28 on a side facing the anode 16. An internal wall 30 is within the housing 26 and has a plurality of holes 35 through gas is able to flow. A plate 32 located within the cathode housing 26 has a rod 34 attached thereto which extends through a wall of the cathode housing and through an opening in the enclosure 11. Specifically, the rod 34 passes through an electrically insulating, resilient seal 36 in the enclosure wall, which prevents gas from leaking around the rod. A plurality of electrically conductive pins 38 are equally spaced in a circle on the plate 32, as shown in FIG. 2, and extend through apertures in the internal wall 30. The pins 38 may be arranged in other geometric patterns on the plate 32 with the housing opening 28 having a corresponding geometric shape. The plate and pin assembly can be moved with respect to the cathode wall 30 by applying force to the rod 34. Such movement varies a distance δ that the pins project from the wall 30 toward the anode 16 thus adjusting the effective pin length. Such pin length adjustment, alters the glow discharge, as well be described.

A metal gas supply tube 40 extends through the insulating seal 36 in a wall of the enclosure 11 and connects to an opening in the cathode housing 26 for supplying a gas to the housing interior as regulated by an external control valve 41. The metal supply tube 40 is connected to the negative terminal of a DC power supply 45 having the positive terminal connected to ground. The enclosure 11 and the anode 16 connected thereto also are connected to ground. As a result of the power supply connection, the cathode 14 is electrically negative with a respect to the anode 16 at a potential which excites the gas from supply tube 40.

As shown in FIG. 1, an analyte in the gas phase is introduced through another tube 46 into the analysis region 22 of chamber 12. The analysis region 22 has a first port 48 extending through the rear wall for a connection to the sample inlet of a conventional mass spectrometer 52 shown in FIG. 3. Another analysis port 50 extends through the front wall, as indicated by dashed lines, for similar connection to a conventional optical spectrometer 54.

During operation of the glow discharge apparatus 10, a rare gas, or a mixture of rare gases, such as helium, neon, argon, krypton and xenon, is continuously fed into the cathode 14 via the supply tube 40. The rare gas, which supports the glow discharge, flows through the discharge region 20 and is pumped from the analysis region 22 through the exhaust port 24. The DC potential applied between the cathode 12 and the anode 16 produces an axial cylinder of plasma 44.

By moving the plate-and pin assembly 32, 38 with respect to the cathode wall 30, the distance δ that the pins 38 project from the wall 30 toward the anode 16 can be varied. When the pins are fully retracted, i.e. δ=0, a glowing cylinder of plasma appears, the diameter of which is approximately equal to the diameter of the opening 28 in the cathode 12. As the pins 38 are extended from wall 30 toward the anode 16, i.e. distance δ increases, the radial glow structure becomes weaker in the central portion of the cylinder. Eventually, the glow is limited to an annular region 42, indicated by the larger stippling in FIG. 1, that is outside the circle on which the pins 38 are located thus defining a cylindrical core 43 enclosed by the pins 38. This plasma core 43, represented by the smaller stippling, is completely dark and comprises low-energy electrons with an electron temperature less than 0.5 eV for example. These low-energy electrons are hereinafter referred to as $e_{slow}$.

The low-energy electrons $e_{slow}$ are extracted from the discharge region 20 into the analysis region 22 by aperture 17 in the anode 16. The third electrode 18 enhances the extraction of electrons into the analysis region 22. The magnetic field B produced by the electromagnet coils 13 and 15 also enhance that electron extraction. The anode aperture 17 is slightly smaller in diameter than the diameter of the circle on which the pins 38 are located, so that only the plasma in the dark inner region will be extracted into the analysis region 22. The higher energy electrons in the outer glow regions strike the anode 16 and do not pass into the analysis region 22. The presence of low energy electrons e $\overline{s}_{low}$ in the analysis region 22 is essential to the production of negative ions. The extracted plasma entering the analysis region 22 also contains metastable excited states of the rare gas or gases, which are herein denoted as $RG^*_m$. The presence of $RG^*_m$ in the analysis region is crucial to the production of positive ions, negative ions and fluorescence, on which the present procedure is based.

The sample M to be analyzed is introduced in a gas phase into the analysis region 22 through the analyte supply tube 46 and interacts with the $RG^*_m$ and the $e_{slow}$ leading to the formation of positive and negative ions which are characteristic of sample M. These interactions also may produce light emission at wavelengths characteristic of that sample M.

With respect to formation of positive ions, if the energy of $RG^*_m$ is higher than the ionization threshold of sample M, then the excitation transfer from $RG^*_m$ to M produces positive ions that are characteristic of the sample, as given by the expression:

$$RG^*_m + M \rightarrow M^+ (\text{or fragment positive ions}) + RG \qquad (1)$$

where RG denotes a rare gas atom in the ground state.

The occurrence of process (1) can be guaranteed by using helium or neon as the rare gas. Metastable states of helium and neon are located at ~20 eV and ~16.7 eV respectively. These energies are higher than the ionization threshold of most chemical species.

The resultant positive ions, characteristic of sample M, then are extracted to a mass spectrometer through the port 48 in the target region and then identified using standard spectroscopic techniques.

Negative ion formation also can be accomplished through excitation transfer from $RG^*_m$ to M to produce electronically excited states of the sample as denoted by M* in the following expression:

$$RG^*_m + M \rightarrow M^* + RG \qquad (2)$$

These electronically-excited states M* interact strongly the low energy electrons $e_{slow}$, thereby producing negative ions that are characteristic of sample M as defined by the process:

$$M^* + e_{slow} \rightarrow \text{negative ions} \qquad (3)$$

Process (3) is highly efficient for electronically-excited states M* located close to the ionization threshold of the sample. This condition will be satisfied from most chemical species when argon or krypton is used as the rare gas. Argon and krypton have metastable state energies of ~11.5 eV and ~10 eV respectively.

The resultant negative ions of the sample are extracted to the mass spectrometer 52 through the port 48 in the analysis region 22 and identified using standard spectroscopic techniques.

The present glow discharge apparatus 10 also can excite the sample to produce light emission for analysis by an optical spectrometer. The excited states, M* produced by process (2) may also emit light as denoted by:

$$M^* \rightarrow M + h\nu \qquad (4)$$

In addition, the excited states M* may decay via dissociation leading to formation of fragments in excited states according to:

$$M^* \rightarrow F_1(*) + F_2(*) + \ldots \qquad (5)$$

where $F_1^{(*)}$, $F_2^{(*)}$ denote fragments of sample M that may be in excited states. Such excited-state fragments may also emit light analogous to process (4) above.

Therefore, depending upon the sample, light emission from its excited states or fragments may occur. By connecting an optical spectrometer to port 50 of the analysis region 22, spectroscopic data can be obtained which is used to identify the sample M. Thus one or more analyses of positive ion formation, negative ion formation, and light emission provide information that is useful in detecting and identifying constituents of the sample being analyzed.

It is possible to obtain all three types of information simultaneously by connecting two mass spectrometers and an optical spectrometer 54 to the analysis region 22. However, preferably most of the information can be obtained using a single mass spectrometer 52 with information on the positive and negative ions being obtained by switching that mass spectrometer operation between positive and negative ion detection modes with a corresponding change in the rare gas flowing through the glow discharge apparatus 10.

Thus, the present glow discharge apparatus 10 serves the analytical capabilities of three different types of instruments combined to provide fast and accurate identification of trace chemicals. The apparatus 10 employs a novel procedure for forming negative ions via electron attachment to electronically excited states which is extremely efficient as compared to negative ion formulation processes used in previous analytical instruments. Another advantage is that the present glow discharge apparatus does directly expose the sample being analyzed to an electric discharge and therefore undesirable destruction of the sample is avoided.

Although the procedure described above analyzed a sample in the gas phase, condensed phase samples can be analyzed by depositing them on a holder that then is placed in the analysis region 22. The sample material is vaporized either by heating the holder or by irradiating the sample with a laser beam.

The foregoing description is directed primarily to preferred embodiments of the invention. Although some attention was given to various alternatives within the scope of the invention, it is anticipated that skilled artisans will likely realize additional alternatives that are now apparent from the disclosure of those embodiments. Accordingly, the scope of the invention should be determined from the following claims and not limited by the above disclosure.

I claim:

1. A glow discharge apparatus for an instrument that analyzes a sample, the apparatus comprising:
   an enclosure forming a chamber;
   an anode within the enclosure and dividing the chamber into a discharge region and an analysis region;
   a gas inlet for introducing a gas into the discharge region;
   a mechanism by which the sample to be analyzed is placed into the analysis region;
   a cathode spaced from the anode within the chamber, wherein an electrical potential applied between the cathode and the anode produces a plasma in the discharge region in which metastable states of the gas are driven into the analysis region where the metastable states excite molecules of the sample; and
   a port opening into the analysis region for coupling to a device that analyzes characteristics of the sample following excitation by the metastable states.

2. The glow discharge apparatus as recited in claim 1 wherein the cathode comprises a plurality of pins projecting in a geometric pattern toward the anode for exciting the gas.

3. The glow discharge apparatus as recited in claim 1 wherein cathode comprises a hollow cathode housing having an opening, a member within the cathode housing, and a plurality of pins projecting in a geometric pattern toward the anode.

4. The glow discharge apparatus as recited in claim 3 wherein the cathode further comprises a wall within the hollow cathode housing with a plurality of apertures through which the plurality of pins extend, wherein a distance δ that the pins project from the wall toward the anode is variable by a user.

5. The glow discharge apparatus as recited in claim 4 wherein the gas inlet is coupled to the cathode to introduce the gas into the hollow cathode housing.

6. The glow discharge apparatus as recited in claim 3 wherein the plurality of pins are arranged in a circular pattern.

7. A glow discharge apparatus for an instrument that analyzes a sample, the apparatus comprising:
   an anode;
   an enclosure forming a chamber which contains the anode wherein the anode defines a discharge region and an analysis region within the chamber;
   a cathode associated with the discharge region and having a plurality of pins projecting in a geometric pattern toward the anode for producing an electric discharge between the cathode and the anode;
   a gas inlet for introducing a gas into the discharge region;
   a mechanism by which the sample to be analyzed is placed into the analysis region so that the sample is bombarded by lower energy electrons extracted from the discharge region; and
   a port opening into the analysis region for coupling to a device that analyzes characteristics of the sample following bombardment by the lower energy electrons.

8. The glow discharge apparatus as recited in claim 7 wherein cathode comprises a driver for varying an electrical discharge length of the pins.

9. The glow discharge apparatus as recited in claim 7 wherein cathode comprises a hollow cathode housing having an opening, and a member within the cathode housing from which the pins extend toward the opening.

10. The glow discharge apparatus as recited in claim 9 wherein the cathode further comprises a wall within the cathode housing and having a plurality of apertures through which the plurality of pins extend wherein a distance δ that the pins project from the wall toward the opening is variable by a user.

11. The glow discharge apparatus as recited in claim 9 wherein the gas inlet is coupled to the cathode to introduce the gas into the cathode housing.

12. The glow discharge apparatus as recited in claim 7 wherein the plurality of pins are arranged in a circular pattern.

13. The glow discharge apparatus as recited in claim 7 wherein the mechanism comprises a port through which the sample in a gas phase is introduced into the enclosure.

14. The glow discharge apparatus as recited in claim 7 further comprising a DC power supply for electrically biasing the cathode and the anode to produce the electric discharge.

15. A glow discharge apparatus for an instrument that analyzes a sample, the apparatus comprising:
   an enclosure forming a reaction chamber;
   a gas outlet for exhausting gas from the enclosure;
   an anode within the enclosure and dividing the chamber into a discharge region and an analysis region, the anode having an aperture therethrough;

a cathode associated with the discharge region and having a plurality of pins projecting in a geometric pattern toward the anode for exciting the gas and producing a plasma discharge between the cathode and the anode wherein electrons with an energy greater than 0.5 eV are substantially confined to the discharge region while lower energy electrons pass into the analysis region through the aperture in the anode;

a gas inlet for introducing a gas into the discharge region;

a mechanism by which the sample to be analyzed is placed into the analysis region; and a port opening into the analysis region for coupling to a spectrometer.

16. The glow discharge apparatus as recited in claim 15 wherein cathode comprises a cathode housing having an opening, a member within the cathode housing and from which the plurality of pins extend toward the opening.

17. The glow discharge apparatus as recited in claim 16 wherein the cathode further comprises a wall within the cathode housing and having a plurality of apertures through which the plurality of pins extend; and a driver for moving the member with respect to the wall to change a distance δ that the pins project from the wall toward the opening.

18. The glow discharge apparatus as recited in claim 16 wherein the gas inlet is coupled to the cathode to introduce the gas into the cathode housing.

19. The glow discharge apparatus as recited in claim 15 wherein the aperture of the anode and the geometric pattern of the plurality of pins are both circular shapes.

20. The glow discharge apparatus as recited in claim 15 wherein the aperture of the anode has a shape of the geometric pattern.

* * * * *